United States Patent
Lee et al.

(10) Patent No.: US 10,232,349 B2
(45) Date of Patent: Mar. 19, 2019

(54) NON-NOBLE METAL-SUPPORTED ZIRCONIUM PHOSPHATE CATALYST FOR GENERATING CYCLIC HYDROCARBON, AND METHOD FOR PREPARING CYCLIC HYDROCARBON BY USING SAME

(71) Applicant: Korea University Research and Business Foundation, Seoul (KR)

(72) Inventors: Kwan Young Lee, Seoul (KR); Geun Ho Han, Seoul (KR); Young-Hoon Cho, Seoul (KR); Min Sung Kim, Seoul (KR); Myung-gi Seo, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/876,895

(22) Filed: Jan. 22, 2018

(65) Prior Publication Data

US 2018/0141026 A1   May 24, 2018

Related U.S. Application Data

(63) Continuation of application No. PCT/KR2015/009846, filed on Sep. 18, 2015.

(30) Foreign Application Priority Data

Jul. 22, 2015   (KR) ........................ 10-2015-0103615

(51) Int. Cl.
*C07C 1/20* (2006.01)
*B01J 23/28* (2006.01)
(Continued)

(52) U.S. Cl.
CPC .............. *B01J 23/28* (2013.01); *B01J 21/06* (2013.01); *B01J 23/74* (2013.01); *B01J 27/16* (2013.01);
(Continued)

(58) Field of Classification Search
CPC ... B01J 23/28; B01J 21/06; B01J 23/74; B01J 27/16; B01J 31/02; B01J 32/00; C07C 1/22; C07C 1/24; C07C 5/10; C07C 13/16
USPC .......................... 502/211, 213, 305, 315, 316
See application file for complete search history.

(56) References Cited

U.S. PATENT DOCUMENTS

| | | | | |
|---|---|---|---|---|
| 3,516,927 A | * | 6/1970 | Jaffe ...................... | B01J 27/188 208/143 |
| 3,544,452 A | * | 12/1970 | Jaffe ...................... | B01J 27/188 208/216 PP |

(Continued)

FOREIGN PATENT DOCUMENTS

| | | | | |
|---|---|---|---|---|
| CN | 10-6582736 | * | 4/2017 | ............ B01J 27/185 |
| JP | 2006-198503 | * | 8/2006 | .............. B01J 23/44 |

(Continued)

OTHER PUBLICATIONS

M. V. Bykova et al., "Ni-based sol-gel catalysts as promising systems for crude bio-oil upgrading: Guaiacol hydrodeoxygenation study." Applied Catalysis B: Environmental 113-114, pp. 296-307. (Year: 2012).*

(Continued)

*Primary Examiner* — Patricia L. Hailey
(74) *Attorney, Agent, or Firm* — Mintz Levin Cohn Ferris Glovsky and Popeo, P.C.; Kongsik Kim; Joohoo Lee

(57) ABSTRACT

This invention relates to a catalyst for preparing a cyclic hydrocarbon, which is a non-noble-metal supported on zirconium phosphate, and to a method of preparing a cyclic hydrocarbon, including preparing a cyclic hydrocarbon from a lignin derivative through hydrodeoxygenation and hydrogenation using the catalyst for preparing a cyclic hydrocarbon.

3 Claims, 4 Drawing Sheets

(51) Int. Cl.
  B01J 21/06      (2006.01)
  B01J 31/02      (2006.01)
  B01J 32/00      (2006.01)
  C07C 13/16      (2006.01)
  B01J 23/74      (2006.01)
  B01J 27/16      (2006.01)
  C07C 1/22       (2006.01)
  C07C 1/24       (2006.01)
  C07C 5/10       (2006.01)

(52) U.S. Cl.
  CPC .............. *B01J 31/02* (2013.01); *B01J 32/00* (2013.01); *C07C 1/22* (2013.01); *C07C 1/24* (2013.01); *C07C 5/10* (2013.01); *C07C 13/16* (2013.01); *C07C 2601/14* (2017.05)

(56) References Cited

U.S. PATENT DOCUMENTS

| | | | | |
|---|---|---|---|---|
| 3,627,672 | A | * | 12/1971 | Kittrell ............ B01J 27/19 208/143 |
| 3,806,445 | A | * | 4/1974 | Henry et al. ....... C10G 67/0445 208/18 |
| 4,240,900 | A | * | 12/1980 | Gilbert ............ C10G 45/54 208/143 |
| 4,647,704 | A | | 3/1987 | Engel et al. |
| 2012/0323056 | A1 | * | 12/2012 | Lee ............... B01J 21/063 585/16 |
| 2013/0060071 | A1 | | 3/2013 | Delledonne et al. |

FOREIGN PATENT DOCUMENTS

| | | | | |
|---|---|---|---|---|
| KR | 10-0587248 | B1 | | 6/2006 |
| KR | 10-2007-0096042 | A | | 10/2007 |
| KR | 10-2007-0096042 | | * 9/2009 | ........... C07D 201/08 |
| KR | 10-2013-0013007 | A | | 2/2013 |
| KR | 10-2013-0013007 | | * 9/2013 | ........... B01J 23/652 |
| KR | 10-2014-0095005 | A | | 7/2014 |
| KR | 10-2014-0095005 | | * 9/2014 | ............ B01J 23/44 |

OTHER PUBLICATIONS

M.V. Bykova et al., "Stabilized Ni-based catalysts for bio-oil hydrotreatment: Reactivity studies using guaiacol." Catalysis Today 220-222, pp. 21-31. (Year: 2014).*

Adid Adep Dwiatmoko et al., "Hydrodeoxygenation of guaiacol on tungstated zirconia supported Ru catalysts." Applied Catalysis A, General 543, pp. 10-16. (Year: 2017).*

Manish Shetty et al., "Reactivity and stability investigation of supported molybdenum oxide catalysts for the hydrodeoxygenation (HDO) of m-cresol." Journal of Catalysis 331, pp. 86-97. (Year: 2015).*

E. A. Roldugina et al., "Hydrodeoxygenation of guaiacol as a model compound of bio-oil in methanol over mesoporous noble metal catalysts." Applied Catalysis A, General 553, pp. 24-35. (Year: 2018).*

Chanakya Ranga et al., "Effect of composition and preparation of supported MoO3 catalysts for anisole hydrodeoxygenation." Chemical Engineering Journal 335, pp. 120-132. (Year: 2018).*

Ivan D. Mora-Vergara et al., "Hydrodeoxygenation of guaiacol using NiMo and CoMo catalysts supported on alumina modified with potassium." Catalysis Today 302, pp. 125-135. (Year: 2018).*

Difan Li et al., "Conversion of biomass to chemicals over zirconium phosphate-based catalysts." Chinese Journal of Catalysis 38, pp. 1784-1793. (Year: 2017).*

Wu, S.K., et al., "Atmospheric Hydrodeoxygenation of Guaiacol over Alumina-, Zirconia, and Silica-Supported Nickel Phosphide Catalysts", ACS Sustainable Chemistry & Engineering (2013), pp. 349-358.

Song, W., et al., "Synergistic effects of Ni and acid sites for hydrogenation and C—O bond cleavage of substituted phenols", Green Chemistry (2015), 17, pp. 1204-1218.

Lee, J., et al., "Aqueous-phase hydrogenation and hydrodeoxygenation of biomass-derived oxygenates with bimetallic catalysts"; Green Chemistry (2014) 16, pp. 708-718.

He, Z., et al, "Hydrodeoxygenation of model compounds and catalytic systems for pyrolysis bio-oils upgrading", Catalysis for Sustainable Energy, (2012) pp. 28-52.

Gutierrez, A., et al., "Hydrodeoxygenation of guaiacol on noble metal catalysts", Catalysis Today, 147 (2009) 239-2436.

Zhao, C. et al., "Aqueous-phase hydrodeoxygenation of bio-derived phenols to cycloalkanes", Journal of Catalysis, 280 (2011) 8-16.

Hong, Y.K., et al., "The catalytic activity of Pd/WOx/y-Al2O3 for hydrodeoxygenation of guaiacol", Applied Catalysis B: Environmental, 150-151 (2014) 438-445.

* cited by examiner

NON-NOBLE METAL-SUPPORTED ZIRCONIUM PHOSPHATE CATALYST FOR GENERATING CYCLIC HYDROCARBON, AND METHOD FOR PREPARING CYCLIC HYDROCARBON BY USING SAME

CROSS-REFERENCES TO RELATED APPLICATIONS

This application is a continuation application of International Application No. PCT/KR2015/009846, filed Sep. 18, 2015, which claims priority to Korean Application No. 10-2015-0103615, filed Jul. 22, 2015. The entire contents of the aforementioned patent applications are incorporated herein by this reference.

TECHNICAL FIELD

The present invention relates to a non-noble-metal supported on zirconium phosphate catalyst for preparing a cyclic hydrocarbon and a method of preparing a cyclic hydrocarbon through hydrodeoxygenation of a lignin derivative including guaiacol using the non-noble-metal supported on zirconium phosphate catalyst.

Recently, biomass is receiving attention as a feedstock for an organic chemical material as well as fuel owing to limited fossil fuel reserves. In particular, lignin, which is a byproduct of currently useful pulp processes, is used as a low-grade fuel through re-burning. Lignin is typically converted into a gas or liquid through pyrolysis and is thus used as a fuel or feedstock. Lignin in a liquid phase is called "bio-oil" and is composed of an aromatic compound having high oxygen content (about 40%).

Accordingly, in order for such bio-oil to serve as a feedstock for a chemical material, it is important to appropriately remove oxygen from the bio-oil. These days, a hydrodeoxygenation (HDO) reaction using a catalyst enables the conversion of a lignin derivative into an aromatic chemical material at high yield through appropriate deoxygenation, and is thus under thorough study because of the high utility thereof.

For example, U.S. Pat. No. 4,647,704 discloses a method of converting lignin into an aromatic material phenol through hydrodeoxygenation. Here, the reaction is carried out using a zero-valent or sulfided tungsten catalyst, a nickel additive, and a silica-alumina or silica-alumina-phosphate support. Furthermore, Korean Patent No. 10-0587248 discloses a method of preparing phenol from benzenediol using a tungsten or molybdenum catalyst including phosphorus, nickel, cobalt, iron, ruthenium, etc., or a cobalt, palladium, nickel or platinum catalyst including zinc, rhenium, selenium, tin, germanium, lead, etc.

Upon deoxygenation, when hydrogen is added, a sulfide catalyst is known to be active. However, in recent papers, sulfur generated from the sulfide catalyst may deactivate the catalyst, may contaminate the product, and requires high-temperature and high-pressure conditions, and thus research into catalysts that obviate sulfur treatment under relatively simple conditions is ongoing (A. Gutierrez et al., Catal. Today vol. 147, 2009, p. 239-246; C. Zhao et al., J. Catal. vol. 280, 2011, p. 8-16).

Currently, there are various documents pertaining to supports and catalysts used to convert a lignin model material such as guaiacol as a reactant in the presence of a catalyst.

In particular, the literature [Y. K. Hong et al. Applied Catalysis B: Environmental 150-151 (2014) 438-445] discloses the final production of cyclohexane through different reaction routes when an acid catalyst is used alone and when an acidic support is added with a noble metal having hydrogenation activity.

[Scheme 1]

(a) HDO Reaction route using acid catalyst

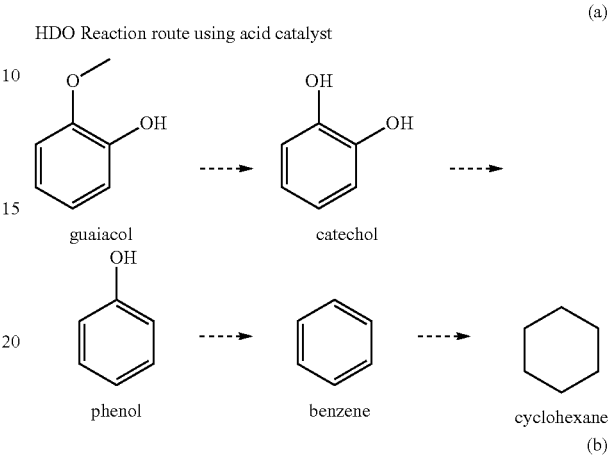

guaiacol → catechol → phenol → benzene → cyclohexane (b) HDO Reaction route using acidic support and noble metal catalyst

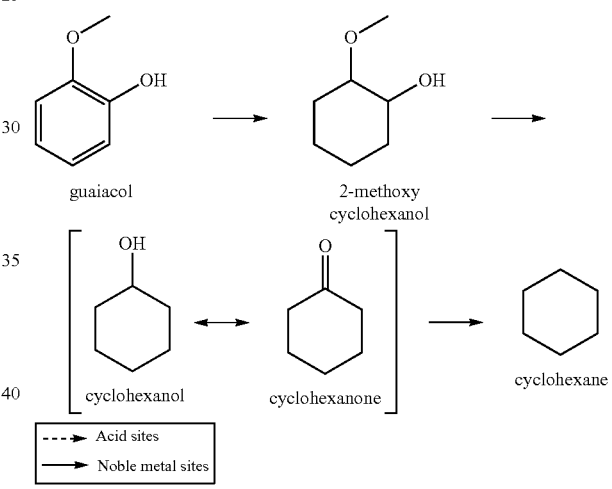

guaiacol → 2-methoxy cyclohexanol → [cyclohexanol ↔ cyclohexanone] → cyclohexane

- - -> Acid sites
——> Noble metal sites

However, the above techniques are problematic because economic benefits are negated due to the use of noble metal, and thus there is a need for methods of economically producing a cyclic hydrocarbon from the lignin derivative through a simpler procedure.

SUMMARY

Accordingly, the present invention is intended to provide the production of a cyclic hydrocarbon (cyclohexane) at high yield through hydrodeoxygenation and hydrogenation of guaiacol, which is a lignin derivative containing aromatic carbon, using a catalyst comprising a zirconium phosphate support and a non-noble metal.

More specifically, the present invention is intended to provide the production of cyclohexane at significantly increased yield (88%) through hydrodeoxygenation and hydrogenation of guaiacol, which is a lignin derivative containing aromatic carbon, using a catalyst comprising a zirconium phosphate support and a non-noble metal due to synergistic effects of the non-noble metal such as cobalt and the zirconium phosphate.

Therefore, the present invention provides a catalyst for preparing a cyclic hydrocarbon, which is a non-noble-metal supported on zirconium phosphate.

In addition, the present invention provides a method of preparing a cyclic hydrocarbon, including preparing a cyclic hydrocarbon from a lignin derivative through hydrodeoxygenation and hydrogenation using the above catalyst.

According to the present invention, the catalyst has no need to treat sulfur that is liable to contaminate a product, and enables the preparation of cyclohexane at high yield under relatively simple conditions.

According to the present invention, when zirconium phosphate is used as a support, cyclohexane can be prepared at remarkably high yield due to the synergistic effects thereof with Ni or Co, compared to the use of typical supports having different acid sites.

According to the present invention, when zirconium phosphate is used as a support, the yield of cyclohexane can be further increased in the presence of a non-noble metal such as Ni or Co than in the presence of a noble metal such as Pd or Pt, typically useful for HDO. In particular, when Co is used, the yield of cyclohexane can be increased up to 88%.

The catalyst of the present invention contains a non-noble metal, thus generating economic benefits compared to existing noble-metal-based catalysts, and also realizing a conversion of 99% in a short reaction time of 2 hr 30 min and a maximum cyclohexane yield of 88%.

DETAILED DESCRIPTION

Figure 1:
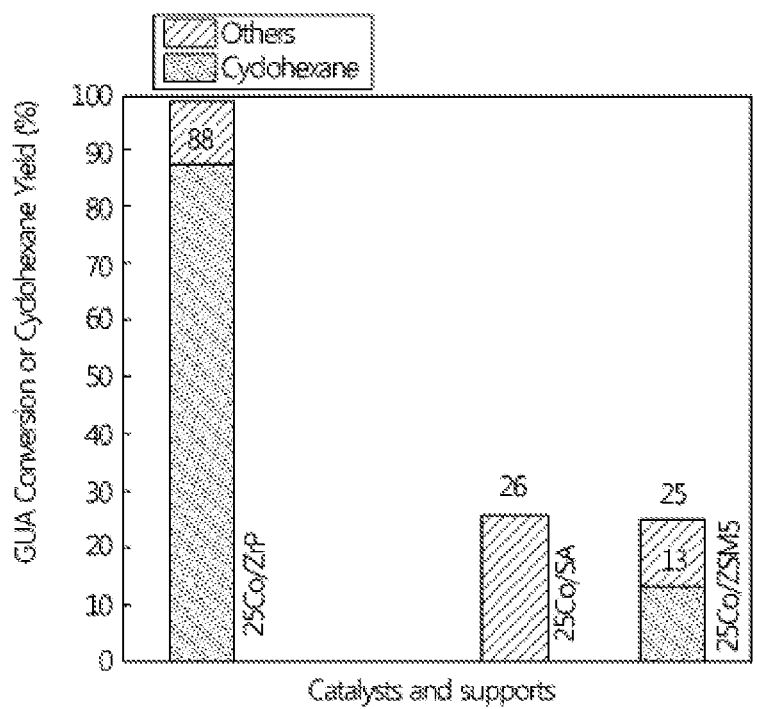
FIG. 1 is a graph showing the results of guaiacol hydrodeoxygenation conversion and cyclohexane yield of comparative supports.

Hereinafter, a detailed description will be given of the present invention.

The present invention addresses a catalyst for preparing a cyclic hydrocarbon, which is a non-noble-metal supported on zirconium phosphate.

The catalyst for preparing a cyclic hydrocarbon according to the present invention is configured such that a non-noble metal is supported on a zirconium phosphate support.

In the present invention, zirconium phosphate, serving as the support, preferably has a P/Zr molar ratio of 1:1 to 1:3.

The non-noble metal preferably includes, but is not necessarily limited to, nickel, cobalt, iron, molybdenum or alloys thereof.

The non-noble metal is preferably supported in an amount of 10 to 40 wt %, and more preferably 20 to 30 wt %, based on the weight of the zirconium phosphate. Within the above amount range, both the metal and the support of the non-noble-metal supported on zirconium phosphate catalyst participate in the reaction. If the amount thereof is less than 10 wt %, active sites of metal may become insufficient. On the other hand, if the amount thereof exceeds 40 wt %, the metal may block the active sites of the support, thus deteriorating the activity of the catalyst.

The catalyst is used for the preparation of a cyclic hydrocarbon from a lignin derivative serving as a reactant.

In addition, the present invention addresses a method of preparing a cyclic hydrocarbon, including preparing a cyclic hydrocarbon from a lignin derivative through hydrodeoxygenation and hydrogenation using the above catalyst.

The lignin derivative is converted into a cyclic hydrocarbon through hydrodeoxygenation and hydrogenation in the above preparation method.

The lignin derivative may include guaiacol, anisole, catechol, phenol or veratrol, and is preferably guaiacol. Here, guaiacol is dissolved in an organic solvent such as n-hexane, n-decane, dodecane, p-xylene, etc.

The cyclic hydrocarbon may include cyclohexane, 1,1'-bicyclohexyl, or the like, and is mainly cyclohexane.

In the preparation method according to the present invention, the cyclic hydrocarbon is preferably prepared under conditions of a reaction temperature of 200 to 400° C., a total pressure of 40 to 70 bar and a reaction time of 1 to 3 hr.

In an embodiment of the present invention, a guaiacol reactant and a non-noble-metal supported on zirconium phosphate are placed in a batch-type reactor, and are then allowed to react at a reaction temperature of 200 to 400° C. and a total pressure of 40 to 70 bar for a reaction time of 1 to 3 hr, whereby guaiacol is converted into cyclohexane, or may also be converted into cyclohexanol and methoxycyclohexanol.

MODE FOR INVENTION

A better understanding of the present invention may be obtained via the following examples, which are merely set forth to illustrate but are not to be construed as limiting the scope of the present invention.

Example 1

Preparation of nCo/ZrP (n=20 wt %, 25 wt %, 30 wt %) Catalyst

Zirconium (IV) hydrogen phosphate (P/Zr molar ratio of 1.2, Sigma Aldrich) was heated at a rate of 1° C./min and fired at 400° C. for 4 hr and thus used as a support. The pore volume of the prepared support was measured through nitrogen adsorption-desorption testing, and cobalt was supported using an incipient wetness method.

The fired zirconium phosphate support was added with cobalt (II) nitrate hexahydrate (Sigma Aldrich) in an amount of n wt % (n=20, 25, 30) based on the weight of the support using an incipient wetness method and then dried at 100° C. for 24 hr. Thereafter, the dried catalyst was fired at 450° C. for 5 hr, thus obtaining a solid catalyst in a powder phase.

Subsequently, the catalyst thus obtained was reduced at 510° C. for 3 hr in a hydrogen atmosphere, thereby yielding a cobalt/zirconium phosphate catalyst in a black powder phase.

Example 2

Preparation of nNi/ZrP (n=20 wt %, 25 wt %, 30 wt %) Catalyst

This catalyst was synthesized in the same manner as in Example 1, with the exception that a nickel precursor (nickel (II) nitrate hexahydrate, Sigma Aldrich) was used in lieu of the cobalt precursor.

Comparative Example 1

Preparation of 2 wt % Pt/ZrP Catalyst

This catalyst was synthesized in the same manner as in Example 1, with the exception that a platinum precursor (tetraammineplatinum (II) nitrate, Sigma Aldrich) was used in lieu of the cobalt precursor.

Comparative Example 2

Preparation of 2 wt % Pd/ZrP Catalyst

This catalyst was synthesized in the same manner as in Example 1, with the exception that a palladium precursor (palladium (II) nitrate hydrate, Sigma Aldrich) was used in lieu of the cobalt precursor.

Comparative Example 3

Preparation of 25 wt % Co/ZSM-5 (11.5) Catalyst

ZSM-5 (Si/Al molar ratio of 11.5, Zeolyst), fired at 500° C. for 5 hr, was used as a support, added with a cobalt precursor in an amount of 25 wt % based on the weight of the ZSM-5 support using an incipient wetness method, and then dried at 100° C. for 24 hr. Thereafter, the dried catalyst was fired at 500° C. for 5 hr, thus obtaining a solid catalyst in a powder phase, which was then reduced at 510° C. for 3 hr in a hydrogen atmosphere, thereby yielding a cobalt/ZSM-5 (11.5) catalyst in a black powder phase.

Comparative Example 4

Preparation of 25 wt % Co/SA (40) Catalyst

This catalyst was synthesized in the same manner as in Comparative Example 3, with the exception that silica-alumina SIRAL (40) ($Al_2O_3$:$SiO_2$=60:40, Sasol), fired at 500° C. for 5 hr, was used as a support.

Experimental Example 1

Figure 3:
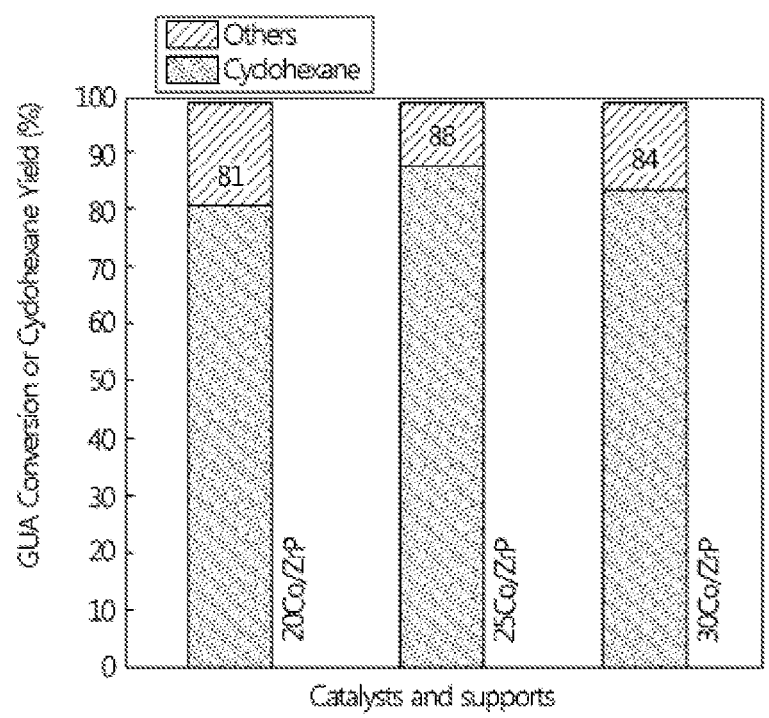
FIG. 3 is a graph showing the cyclohexane yield and conversion as the results of guaiacol hydrodeoxygenation and hydrogenation depending on the amount of cobalt that is supported.

Preparation of Cyclohexane through Hydrodeoxygenation and Hydrogenation of Lignin Derivative Guaiacol Using the above Catalyst 50 ml of a dodecane solvent was added with 0.2 M guaiacol and 0.5 g of the catalyst (nCo/ZrP) of Example 1, and the resulting mixture was placed in a batch-type reactor and heated to 300° C., and the total pressure was maintained at 70 bar using a hydrogen gas, after which the reaction was carried out at 300 rpm for 2 hr 30 min, thus preparing cyclohexane. The temperature was then decreased to room temperature, and guaiacol conversion and a yield of a final product, namely cyclohexane, were measured. The results are shown in FIG. 3.

The guaiacol conversion and the cyclohexane yield were calculated using Equations 1 and 2 below.

$$X_{GUA}(\%) = \frac{n(GUA)_{initial} - n(GUA)_{final}}{n(GUA)_{initial}} \times 100 \quad \text{Equation 1}$$

$$Y_{Cyclohexane}(\%) = \frac{n(\text{Product})_{Cyclohexane}}{n(GUA)_{initial}} \times 100 \quad \text{Equation 2}$$

Experimental Example 2

Figure 4:
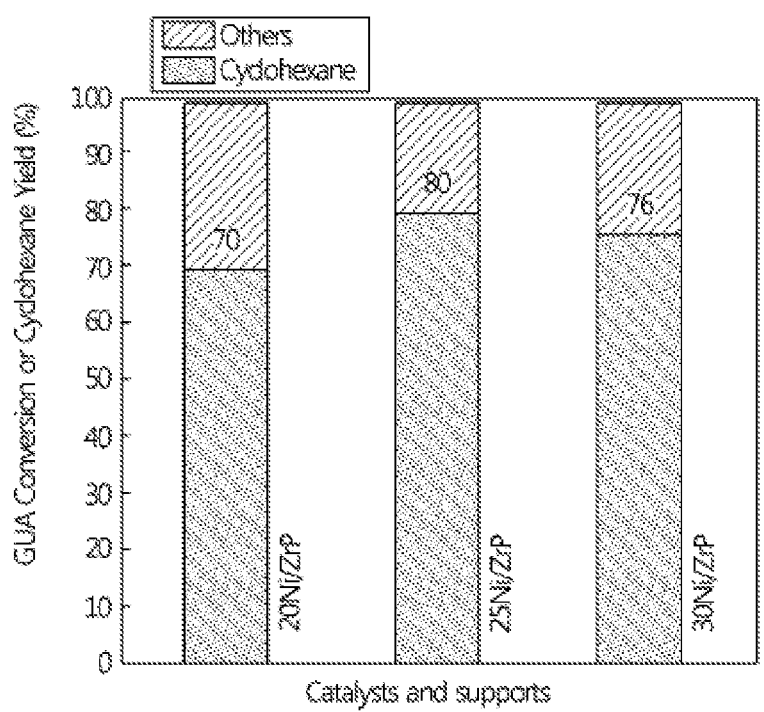
FIG. 4 is a graph showing the cyclohexane yield and conversion as the results of guaiacol hydrodeoxygenation and hydrogenation depending on the amount of nickel that is supported.

Cyclohexane was prepared in the same manner as in Test Example 1, with the exception that the catalyst (nNi/ZrP) of Example 2 was used. Thereafter, the temperature was decreased to room temperature, and the yield of a final product was measured. The results are shown in FIG. 4.

Comparative Experimental Example 1

Figure 2:
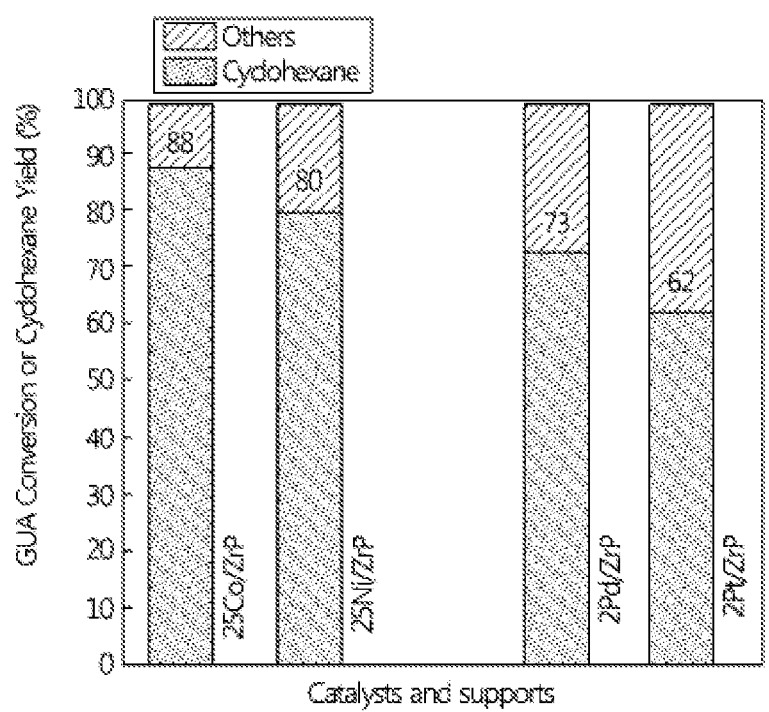
FIG. 2 is a graph showing the results of guaiacol hydrodeoxygenation conversion and cyclohexane yield of comparative metals.

Cyclohexane was prepared in the same manner as in Test Example 1, with the exception that the catalyst (2 wt % Pt/ZrP) of Comparative Example 1 was used. Thereafter, the temperature was decreased to room temperature, and the yield of a final product was measured. The results are shown in FIG. 2.

Comparative Experimental Example 2

Cyclohexane was prepared in the same manner as in Test Example 1, with the exception that the catalyst (2 wt % Pt/ZrP) of Comparative Example 2 was used. Thereafter, the temperature was decreased to room temperature, and the yield of a final product was measured. The results are shown in FIG. 2.

Comparative Experimental Example 3

Cyclohexane was prepared in the same manner as in Test Example 1, with the exception that the catalyst (25 wt % Co/ZSMS (11.5)) of Comparative Example 3 was used. Thereafter, the temperature was decreased to room temperature, and the yield of a final product was measured. The results are shown in FIG. 1.

Comparative Experimental Example 4

Cyclohexane was prepared in the same manner as in Test Example 1, with the exception that the catalyst (25 wt % Co/SA (40)) of Comparative Example 4 was used. Thereafter, the temperature was decreased to room temperature, and the yield of a final product was measured. The results are shown in FIG. 1.

Based on the test results, as shown in FIG. 1, when the zirconium phosphate support according to the present invention was used, a rather high cyclohexane yield was obtained compared to when using typical supports having different acid sites, such as SIRAL (40) ($Al_2O_3$:$SiO_2$=60:40, Sasol) and ZSM-5 (Si/Al ratio of 11.5, Zeolyst).

As shown in FIG. 2, when the zirconium phosphate support according to the present invention was used, higher cyclohexane yield was obtained in the presence of a non-noble metal such as Ni or Co than in the presence of a noble metal such as Pd or Pt, typically useful for HDO. In particular, the use of Co led to a cyclohexane yield of 88%.

Based on the test results, according to the present invention, a conversion of 99% was achieved in a short reaction time of 2 hr 30 min, and a maximum cyclohexane yield was measured to be 88%.

According to the present invention, the catalyst has no need to treat sulfur that is liable to contaminate a product, and enables the production of cyclohexane at high yield under relatively simple conditions.

The invention claimed is:

1. A method of preparing a cyclic hydrocarbon, comprising preparing a cyclic hydrocarbon from a lignin derivative through hydrodeoxygenation and hydrogenation using a catalyst, wherein the catalyst is a non-noble-metal supported on zirconium phosphate.

2. The method of claim 1, wherein the hydrodeoxygenation and hydrogenation are carried out under conditions of a reaction temperature of 200 to 400° C., a total pressure of 40 to 70 bar, and a reaction time of 1 to 3 hr.

3. The method of claim 1, wherein the lignin derivative is guaiacol, anisole, catechol, phenol or veratrol.

* * * * *